(12) United States Patent
Garr et al.

(10) Patent No.: US 9,878,930 B1
(45) Date of Patent: Jan. 30, 2018

(54) SYSTEMS AND METHODS FOR INSTALLING DIGESTER BALLAST

(71) Applicant: WesTech Engineering, Inc., Salt Lake City, UT (US)

(72) Inventors: Tyler D. Garr, Sandy, UT (US); Chad T. Allen, Herriman, UT (US)

(73) Assignee: WesTech Engineering, Inc., Salt Lake City, UT (US)

( * ) Notice: Subject to any disclaimer, the term of this patent is extended or adjusted under 35 U.S.C. 154(b) by 483 days.

(21) Appl. No.: 14/508,957

(22) Filed: Oct. 7, 2014

(51) Int. Cl.
  *C02F 3/28* (2006.01)
  *F17B 1/10* (2006.01)
  *C12M 1/107* (2006.01)
  *B23P 17/04* (2006.01)

(52) U.S. Cl.
  CPC ........... *C02F 3/2866* (2013.01); *C12M 21/04* (2013.01); *C12M 23/36* (2013.01); *F17B 1/10* (2013.01); *B23P 17/04* (2013.01)

(58) Field of Classification Search
  CPC ... F17B 1/10; F17B 1/14; F17B 1/013; C12M 21/04; C12M 23/36; C12M 23/38; C12M 23/46; C02F 3/28; C02F 3/2866
  See application file for complete search history.

(56) References Cited

U.S. PATENT DOCUMENTS

| | | |
|---|---|---|
| 251,245 A | 12/1881 | King |
| 819,665 A | 5/1904 | Lowe |
| 1,037,904 A | 9/1912 | Hawver |
| 1,989,589 A | 1/1935 | Fischer et al. |
| 2,050,686 A | 8/1936 | Wiggins |
| 2,497,047 A | 2/1950 | Frank et al. |
| RE23,417 E | 10/1951 | Prager |
| 2,882,137 A | 4/1959 | Wiggins |
| 2,905,424 A | 9/1959 | Snow |
| 3,249,251 A | 5/1966 | Nachshen |
| 3,288,295 A | 11/1966 | Kelly |
| 3,535,236 A | 10/1970 | Travis |
| 3,797,607 A * | 3/1974 | Gargasz .................... E04G 5/06 182/120 |
| 3,802,620 A | 4/1974 | Ferrara |
| 4,378,437 A | 3/1983 | Cook |
| 4,391,705 A | 7/1983 | Cook et al. |
| 4,710,292 A | 12/1987 | DeVos |
| 4,917,250 A | 4/1990 | Barbieri et al. |
| 5,052,648 A * | 10/1991 | Landau ................ A47B 43/006 108/149 |
| 5,092,482 A | 3/1992 | Wight et al. |
| 5,238,844 A | 8/1993 | Wight et al. |

(Continued)

*Primary Examiner* — Christopher M Koehler
(74) *Attorney, Agent, or Firm* — Austin Rapp

(57) ABSTRACT

An enhanced apparatus system and method may be used to facilitate the construction of a processing tank such as an anaerobic digester. The kit may include a cover assembly that can be assembled to form a cover for the processing tank, a side wall assembly that can be assembled to form a side wall for the processing tank, and a plurality of ballast support assemblies. Each ballast support assembly may have a retracted configuration in which the ballast support assembly avoids significantly impeding vertical motion of the ballast block from an initial ballast location to a final ballast location, and a deployed configuration in which the ballast block can be supported by the ballast support assembly in the final ballast location.

20 Claims, 6 Drawing Sheets

(56) References Cited

U.S. PATENT DOCUMENTS

| | | | |
|---|---|---|---|
| 5,423,895 A | 6/1995 | Wight et al. | |
| 5,480,058 A | 1/1996 | Hutchins | |
| 5,794,385 A | 8/1998 | Donovan | |
| 6,224,029 B1 | 5/2001 | Marble et al. | |
| 6,247,278 B1 | 6/2001 | Rysgaard | |
| 8,281,543 B2 | 10/2012 | Cook et al. | |
| 8,607,995 B1 | 12/2013 | Mladinich | |
| 2004/0232148 A1* | 11/2004 | Vera | B65D 88/34 220/216 |
| 2005/0258117 A1 | 11/2005 | Drake | |
| 2009/0100787 A1* | 4/2009 | Cook | C12M 21/04 52/745.06 |
| 2012/0097629 A1 | 4/2012 | Brisendine | |

* cited by examiner

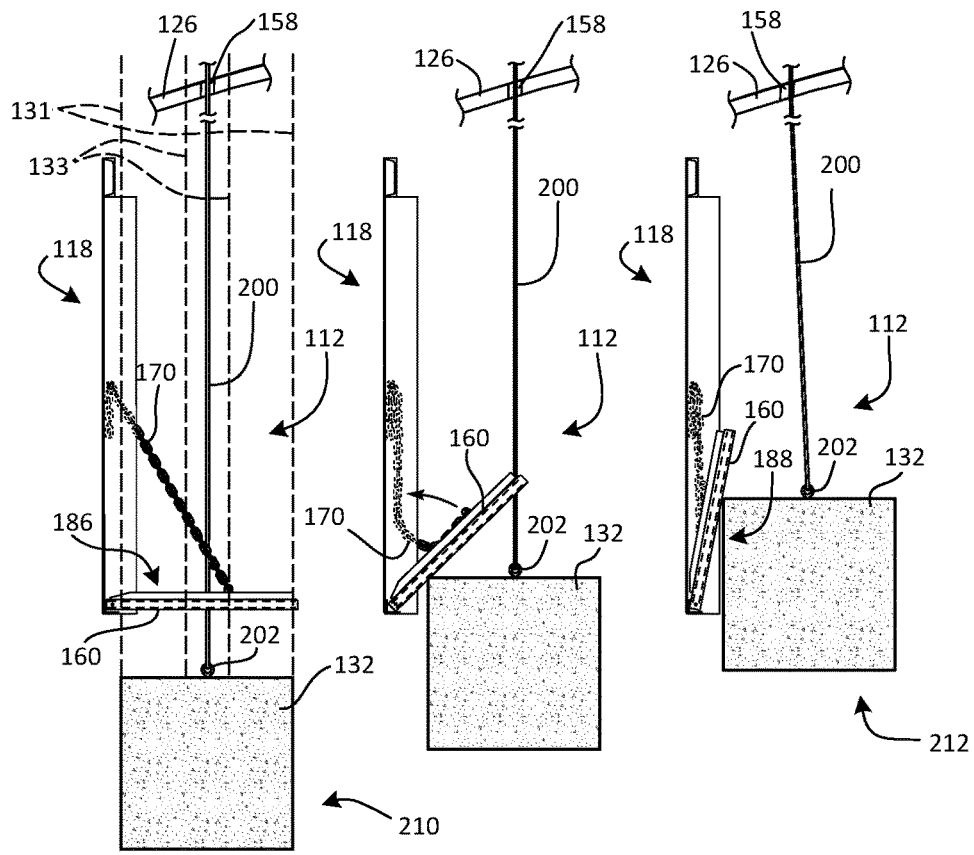
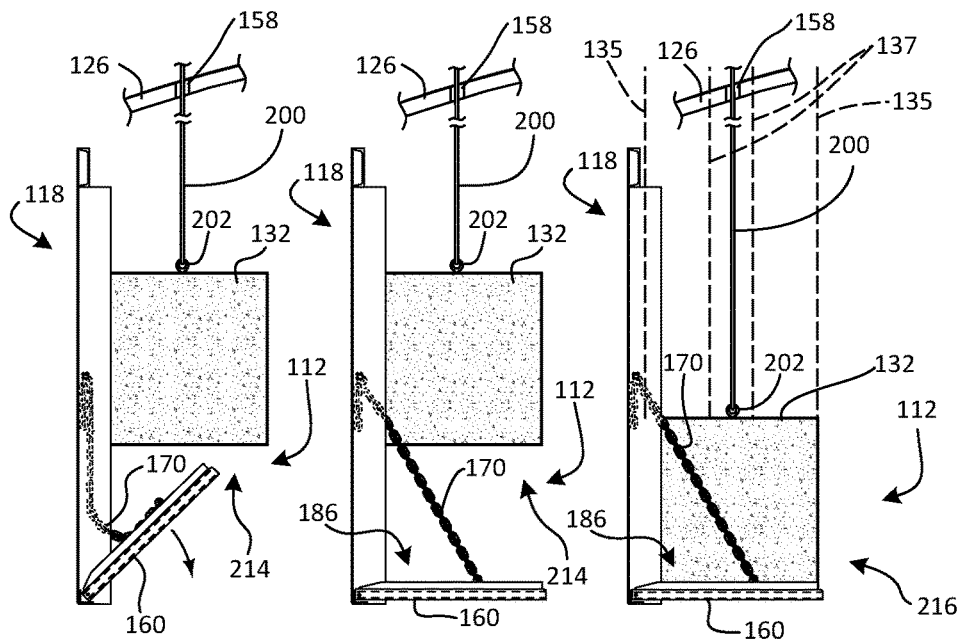
Fig. 5A  Fig. 5B  Fig. 5C
Fig. 5D  Fig. 5E  Fig. 5F

SYSTEMS AND METHODS FOR INSTALLING DIGESTER BALLAST

TECHNICAL FIELD

The present invention relates generally to an apparatus and a method for installing ballast in a processing tank such as a digester.

BACKGROUND

A wide variety of processing tanks are used in various industrial and municipal applications. Some processing tanks, known as anaerobic digesters, may be used for processing sewage and/or other materials in an oxygen-free environment. Such processing tanks often include the use of ballast blocks to maintain a desired level of gas pressure within the tank. Such ballast blocks are typically quite large and heavy, and can be difficult to maneuver into place with existing methods.

Accordingly, improved methods for installing digester ballast are desirable. Improved systems for constructing processing tanks that facilitate ballast installation are also desirable.

SUMMARY

Embodiments of the disclosed subject matter are provided below for illustrative purposes and are in no way limiting of the claimed subject matter.

In some embodiments, a system for facilitating construction of a processing tank may include a cover assembly that can be assembled to form a cover that defines an upper barrier for the processing tank, a side wall assembly that can be assembled to form a side wall connectable to the cover, and a first ballast support assembly. The first ballast support assembly may include a first arm connectable to the side wall assembly such that the first arm is pivotable between a first horizontal orientation and a first upwardly-angled orientation, a second arm pivotably connectable to the side wall assembly such that the second arm is pivotable between a second horizontal orientation and a second upwardly-angled orientation, a first flexible member with a first proximal end connectable to the side wall assembly and a first distal end connectable to the first arm, and a second flexible member with a second proximal end connectable to the side wall assembly and a second distal end connectable to the second arm. With the first arm in the first horizontal orientation, the first flexible member may be tensioned to restrict pivoting of the first arm below the first horizontal orientation. With the second arm in the second horizontal orientation, the second flexible member may be tensioned to restrict pivoting of the second arm below the second horizontal orientation. With the first arm in the first upwardly-angled orientation and the second arm in the second upwardly-angled orientation, the first ballast support assembly may not significantly block vertical motion of a first ballast block from an initial ballast location to a final ballast location offset substantially directly vertically from the initial ballast location. With the first arm in the first horizontal orientation and the second arm in the second horizontal orientation, the first ballast support assembly may be positioned to retain the first ballast block in the final ballast location. The cover assembly may include a plurality of cover panels, each of which has a generally sectoral shape. The cover panels may be attachable together to form the cover such that the cover has a generally circular shape. The side wall assembly may include a plurality of wall panels, each of which has a generally arcuate shape. The wall panels may be attachable together to form the side wall such that the side wall has a generally tubular shape. The system may further comprise a slide guide assembly having a plurality of slide guides securable to an outer wall. The plurality of sliders may also be securable to the side wall and/or the cover. Each of the plurality of sliders may slidably engage at least one of the slide guides. The cover and the first ballast support assembly can be coupled to the side wall. Accordingly, when the cover and the first ballast support assembly are secured to the side wall and when each of the plurality of sliders are secured to the side wall and/or the cover and slidably engage at least one of the slide guides, the cover and the first ballast support assembly may move vertically with the side wall relative to the outer wall. The system may further include a plurality of additional ballast support assemblies, which may include a plurality of additional first arms connectable to the side wall assembly such that the plurality of additional first arms are pivotable between a plurality of additional first horizontal orientations and a plurality of first upwardly-angled orientations, a plurality of additional second arms connectable to the side wall assembly such that the plurality of additional second arms are pivotable between a plurality of additional second horizontal orientations and a plurality of second upwardly-angled orientations, a plurality of additional first flexible members connectable to the plurality of additional first arms and the side wall assembly, and a plurality of additional second flexible members connectable to the plurality of additional second arms and the side wall assembly. With the plurality of additional first arms in the plurality of additional first horizontal orientations, the plurality of additional first flexible members may be tensioned to restrict pivoting of the plurality of additional first arms below the plurality of additional first horizontal orientations. With the plurality of additional second arms in the plurality of additional second horizontal orientations, the plurality of additional second flexible members may be tensioned to restrict pivoting of the plurality of additional second arms below the plurality of additional second horizontal orientations.

The cover assembly may have an aperture positionable at a location within a vertical extension of both the initial ballast location and the final ballast location such that, with the side wall assembly oriented vertically and the cover assembly secured above the side wall assembly, a flexible member lowered through the aperture can lift the first ballast block substantially vertically to move the first ballast block from the initial ballast location to the final ballast location.

The first ballast support assembly may be movably connectable to the side wall assembly such that gravity exerts force on the first arm tending to move the first arm from the first upwardly-angled orientation to the first horizontal orientation and exerts force on the second arm tending to move the second arm from the second upwardly-angled orientation to the second horizontal orientation. The first ballast support assembly may be movably connected to the side wall assembly such that motion of the first ballast block from the initial ballast location to a retraction ballast location causes the first ballast block to abut the first ballast support assembly to move the first arm from the first horizontal orientation to the first upwardly-angled orientation and move the second arm from the second horizontal orientation to the second upwardly-angled orientation. The first ballast support assembly may further be movably connectable to the side wall such that motion of the first ballast block from the retraction ballast location to a deployment ballast location above the retraction ballast location causes the first arm to return to the first horizontal orientation and causes the second arm to return to the second horizontal orientation. With the first arm in the first horizontal orientation and the second arm in the second horizontal orientation, the first ballast support assembly may be positioned to receive and retain the first ballast block in response to motion of the first ballast block from the deployment ballast location to the final ballast location.

According to one embodiment, a system for facilitating construction of a processing tank may include a cover assembly that can be assembled to form a cover that defines an upper barrier for the processing tank, a side wall assembly that can be assembled to form a side wall securable to the cover, and a first ballast support assembly movably connectable to the side wall assembly such that, with the side wall assembly oriented vertically, the first ballast support assembly has, relative to the side wall assembly, a retracted configuration and a deployed configuration. In the retracted configuration, the first ballast support assembly may not significantly block vertical motion of a first ballast block from an initial ballast location to a final ballast location offset substantially directly vertically from the initial ballast location. In the deployed configuration, the first ballast support assembly may be positioned to retain the first ballast block in the final ballast location.

The cover assembly may include a plurality of cover panels, each of which has a generally sectoral shape. The cover panels may be attachable together to form the cover such that the cover has a generally circular shape. The side wall assembly may include a plurality of wall panels, each of which has a generally arcuate shape. The wall panels may be attachable together to form the side wall such that the side wall has a generally tubular shape.

The system may further comprise a slide guide assembly having a plurality of slide guides securable to an outer wall. The plurality of sliders may be securable to the side wall and/or the cover. Each of the plurality of sliders may slidably engage at least one of the slide guides. The cover and the first ballast support assembly can be coupled to the side wall. Accordingly, when the cover and the first ballast support assembly are secured to the side wall and when each of the plurality of sliders are secured to the side wall and/or the cover and slidably engage at least one of the slide guides, the cover and the first ballast support assembly may move vertically with the side wall relative to the outer wall. The system may further include a plurality of additional ballast support assemblies, each of which is movably connectable to the side wall assembly such that, with the side wall assembly oriented vertically, each of the additional ballast support assemblies has the retracted configuration and the deployed configuration relative to an additional ballast block of a plurality of additional ballast blocks of the processing tank.

The cover assembly may have an aperture positionable at a location within a vertical extension of both with the initial ballast location and the final ballast location such that, with the side wall assembly oriented vertically and the cover assembly secured above the side wall assembly, a distal end of a flexible member lowered through the aperture can lift the first ballast block substantially vertically to move the first ballast block from the initial ballast location to the final ballast location.

The first ballast support assembly may be movably connected to the side wall assembly such that motion of the first ballast block from the initial ballast location to the final ballast location causes the first ballast block to abut the first ballast support assembly to move the first ballast support assembly from the deployed configuration to the refracted configuration.

The first ballast support assembly may be movably connectable to the side wall assembly such that gravity exerts force on the first ballast support assembly tending to move the first ballast support assembly from the retracted configuration to the deployed configuration. The first ballast support assembly may further be movably connectable to the side wall such that motion of the first ballast block from the final ballast location to a deployment ballast location above the final ballast location causes the first ballast support assembly to return to the deployed configuration. In the deployed configuration, the first ballast support assembly may be positioned to receive and retain the first ballast block in response to motion of the first ballast block from the deployment ballast location to the final ballast location.

The first ballast support assembly may include a first arm pivotably connectable to the side wall assembly such that the first arm is in a first horizontal orientation in the deployed configuration, and in a first upwardly-angled orientation in the retracted configuration.

The first ballast support assembly may further include a first flexible member with a first proximal end connectable to the side wall assembly, and a first distal end connectable to the first arm. In the deployed configuration, the first flexible member may be tensioned to restrict pivoting of the first arm below the first horizontal orientation.

The first ballast support assembly may further include a second arm pivotably connectable to the side wall assembly such that the second arm is in a second horizontal orientation in the deployed configuration, and in a second upwardly-angled orientation in the retracted configuration. The first ballast support assembly may further include a second flexible member with a first proximal end connectable to the side wall assembly and a first distal end connectable to the first arm. In the deployed configuration, the first flexible member may be tensioned to restrict pivoting of the first arm below the second horizontal orientation.

According to one embodiment, a method for constructing a processing tank may include the steps of at least partially assembling a cover assembly to form at least part of a cover that defines an upper barrier for the processing tank, at least partially assembling a side wall assembly to form at least part of a side wall connectable to the cover, raising a first ballast block from an initial ballast location to a retraction ballast location, moving a first ballast support assembly from a deployed configuration to a retracted configuration, raising the first ballast block from the retraction ballast location to a deployment ballast location, moving the first ballast support assembly from the retracted configuration back to the deployed configuration, and lowering the first ballast block from the deployment ballast location to a final ballast location such that the first ballast support assembly retains the first ballast block in the final ballast location.

Moving the first ballast support assembly from the deployed configuration to the retracted configuration may include, in response to moving the ballast block to the retraction ballast location, abutting the first ballast support assembly with the first ballast block to move the first ballast support assembly to the retracted configuration.

The first ballast support assembly may be movably connectable to the side wall assembly such that gravity exerts force on the first ballast support assembly tending to move the first ballast support assembly from the retracted configuration to the deployed configuration. Moving the first ballast support assembly from the retracted configuration back to the deployed configuration may include, in response to raising the first ballast block from the retraction ballast location to the deployment ballast location, withdrawing the first ballast block from abutment with the first ballast support assembly to permit motion of the first ballast support assembly back to the deployed configuration.

The cover assembly may include an aperture. At least partially assembling the cover assembly may include positioning the aperture at a location within a vertical extension of both the initial ballast location and the final ballast location. The method may further include, prior to raising the first ballast block from the initial ballast location to the retraction ballast location, lowering a distal end of a flexible member through the aperture and securing the distal end to the first ballast block. Raising the first ballast block from the initial ballast location to the retraction ballast location may include tensioning the flexible member to pull the first ballast block substantially vertically to the final ballast location.

The first ballast support assembly may include a first arm pivotably connectable to the side wall assembly and a first flexible member with a first proximal end connectable to the side wall assembly and a first distal end connectable to the first arm. Moving the first ballast support assembly from the deployed configuration to the retracted configuration may include moving the first arm from a first horizontal orientation, in which the first flexible member is tensioned to restrict pivoting of the first arm below the first horizontal orientation, to a first upwardly-angled orientation.

The first ballast support assembly may further include a second arm pivotably connectable to the side wall assembly and a second flexible member with a second proximal end connectable to the side wall assembly and a second distal end connectable to the second arm. Moving the first ballast support assembly from the deployed configuration to the retracted configuration may include moving the second arm from a second horizontal orientation, in which the second flexible member is tensioned to restrict pivoting of the second arm below the second horizontal orientation, to a second upwardly-angled orientation.

BRIEF DESCRIPTION OF DRAWINGS

Exemplary embodiments of the invention will become more fully apparent from the following description and appended claims, taken in conjunction with the accompanying drawings. These drawings depict only exemplary embodiments and are, therefore, not to be considered limiting of the invention's scope. Accordingly, the exemplary embodiments of the invention will be described with additional specificity and detail through use of the accompanying drawings in which:

FIGS. 5A-5F are side elevation views of one of the ballast support assemblies of the processing tank of FIG. 1, with a ballast block in various locations as it is moved from an initial ballast location in FIG. 5A to a final ballast location in FIG. 5F.

Figure 1:
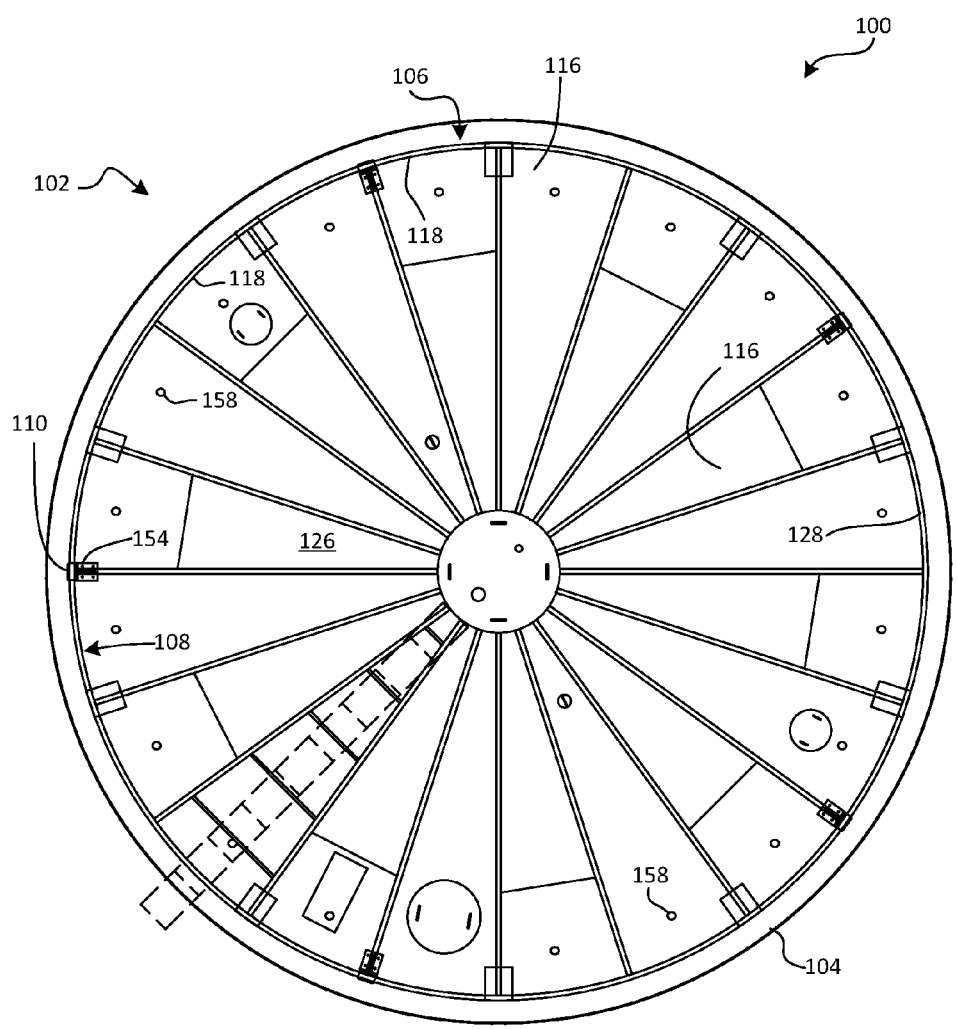
FIG. 1 is a plan view of a processing tank according to one embodiment of the invention.

In accordance with common practice, the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus (e.g., a device) or method. Finally, like reference numerals may be used to denote like features throughout the specification and figures.

DETAILED DESCRIPTION

Various aspects of the disclosure are described below. It should be apparent that the teachings herein may be embodied in a wide variety of forms and that any specific structure, function, or both being disclosed herein is merely representative. Based on the teachings herein, one skilled in the art should appreciate that an aspect disclosed herein may be implemented independently of any other aspects and that two or more of these aspects may be combined in various ways. For example, an apparatus may be implemented or a method may be practiced using any number of aspects set forth herein. In addition, such an apparatus may be implemented or such a method may be practiced using other structure and functionality not set forth herein, but which is known to one of skill in the art.

The word "exemplary" is used exclusively herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

FIG. 1 is a plan view of a processing tank 100 according to one embodiment of the invention. The processing tank 100 may be any type of tank with an expandable profile. According to some embodiments, the processing tank 100 may be an anaerobic digester or the like. The processing tank 100 may be constructed through the use of a system 102, which may include various modules incorporated into the structure of the processing tank 100.

Figure 2:
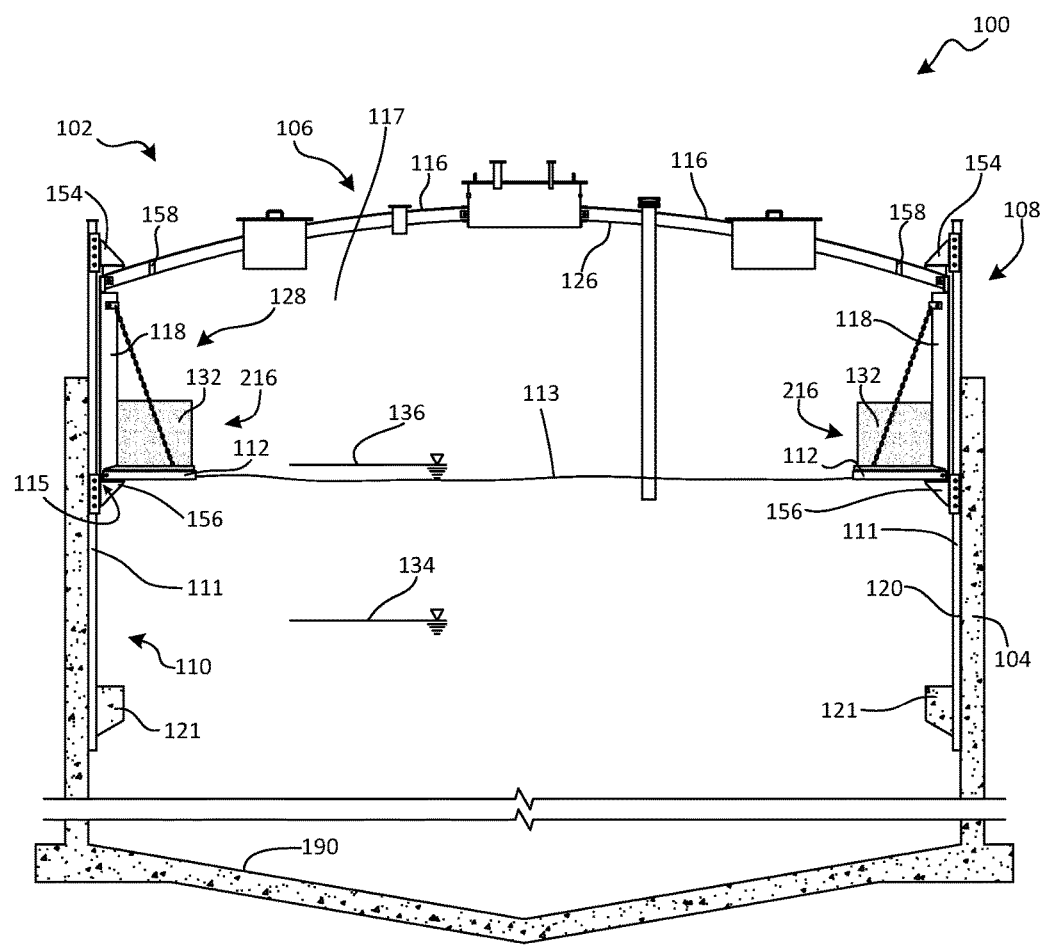
FIG. 2 is a side elevation, section view of the processing tank of FIG. 1.

FIG. 2 is a side elevation, section view of the processing tank 100 of FIG. 1. As shown, the processing tank 100 may include an outer wall 104, which may be formed of concrete or the like. The outer wall 104 may encircle various components of the system 102, and may optionally serve as a bottom wall and/or lower portion of the side wall for the processing tank 100. In order to construct the processing tank 100, the outer wall 104 may first be formed, and then the system 102 may be assembled in-situ, within and/or outside of the outer wall 104.

Referring to FIGS. 1 and 2, the system 102 may include a cover assembly 106, a side wall assembly 108, a slide guide assembly 110, one or more sliders 154, 156 and a plurality of ballast support assemblies 112. The cover assembly 106 may include a plurality of cover panels 116, each of which may have a sectoral shape. When secured together, the cover panels 116 of the cover assembly 106 may define a cover 126 of the system 102. The cover 126 may have a generally discoid shape, and may be contoured to define a dome-like shape.

Similarly, the side wall assembly 108 may include a plurality of side wall panels 118, each of which may have an arcuate shape defining a sectoral portion of a tube. When secured together, the side wall panels 118 of the side wall assembly 108 may define a side wall 128 of the system 102. The side wall 128 may have a generally tubular shape, and may have an inner diameter similar to the outer diameter of the cover 126 so that the top end of the side wall 128 can be secured to the periphery of the cover 126 to define a generally gastight seal.

The system 102 may further comprise a slide guide assembly 110 having a plurality of slide guides 111 securable to an interior surface 120 of an outer wall 104. The plurality of sliders 154, 156 may be securable to the side wall 128 and/or the cover 126 as well. Each of the plurality of sliders 154, 156 may slidably engage at least one of the slide guides 111. The cover 126 and the ballast support assembly 112 may be coupled to the side wall 128. Accordingly, when the cover 126 and the ballast support assembly 112 are secured to the side wall 128 and when each of the plurality of sliders 154,156 are secured to the side wall 128 and/or the cover 126 and slidably engage at least one of the slide guides 111, the cover 126 and the ballast support assembly 112 may move vertically with the side wall 128. One or more stops 121 may be used to limit the downward movement of the cover 126 and the ballast support assembly 112.

In one embodiment, the bottom edge 115 of the side wall 128 may be disposed within the liquid 113 such that the surface of the liquid 113, the side wall 128 and the cover assembly 106 define an enclosed, gastight chamber 117 for retaining gas emitted by the liquid 113. So long as the bottom edge 115 of the side wall 128 is disposed within the liquid 113, the side wall 128 and the cover assembly 106 may move upward or downward to accommodate an increase or decrease in the volume of gas within the enclosed chamber 117.

It may be desirable to maintain a relatively consistent operating pressure within the processing tank 100, regardless of the current stage of processing of the material contained within the processing tank 100. Thus, a plurality of ballast blocks 132 may be coupled to the side wall 128 such that the side wall 128 carries the weight of the ballast blocks 132. Then, when the pressure of gases within the processing tank 100 increases to a point sufficient to exert upward pressure on the cover 126 that exceeds the combined weight of the ballast blocks 132, the side wall 128, and the cover 126, the ballast blocks 132, the side wall 128, and the cover 126 may all move upward within the slide guide assembly 110 to allow the processing tank 100 to expand. Thus, the processing tank 100 may be designed to contain a mixture of liquid and gaseous materials, with a liquid level ranging from a low liquid level 134 to a high liquid level 136, as illustrated in FIG. 2.

The processing tank 100 may include two ballast blocks 132 for each side wall panel 118. The ballast blocks 132, as illustrated in FIG. 2, are shown in a final ballast position 216. Each of the ballast blocks 132 may have a trapezoidal shape such that, when arranged in a circular pattern, the ballast blocks 132 cooperate to define a ring-like shape. The shape of the ballast blocks 132 is more clearly shown in FIG. 6. In various embodiments, each of the ballast blocks 132 may encompass several cubic feet in volume; thus, each ballast block 132 may weigh multiple tons. Accordingly, the process of getting the ballast blocks 132 into place on the side wall 128 may require the use of heavy equipment. Prior art methods of positioning ballast blocks tend to require too much maneuvering of the ballast blocks, resulting in the need for cumbersome and sometimes dangerous procedures. The ballast support assemblies 112 of the present invention enable methods of securing the ballast blocks 132 to the side wall 128 that reduce the need for maneuvering, as will be shown and described in connection with FIGS. 3-5.

Figure 3:
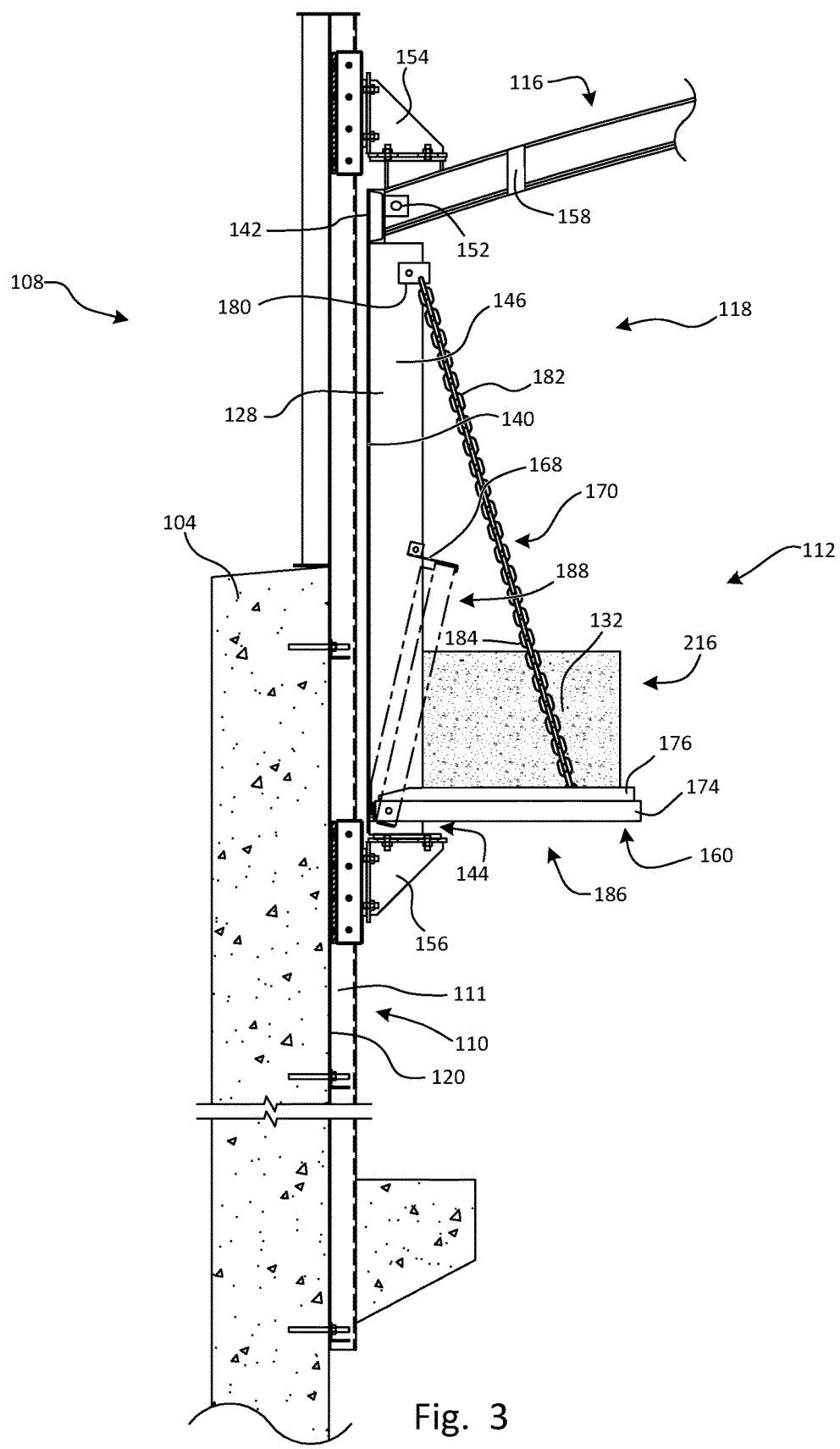
FIG. 3 is an enlarged side elevation, section view of a portion of the processing tank of FIG. 1.

FIG. 3 is an enlarged side elevation, section view of a portion of the processing tank 100 of FIG. 1. The section view of FIG. 3 illustrates a portion of the outer wall 104 along with the slide guide assembly 110, one of the side wall panels 118 of the side wall assembly 108, and one of the cover panels 116 of the cover assembly 106. One of the ballast blocks 132 is also shown retained in its final ballast location relative to the side wall panel 118.

Figure 4:
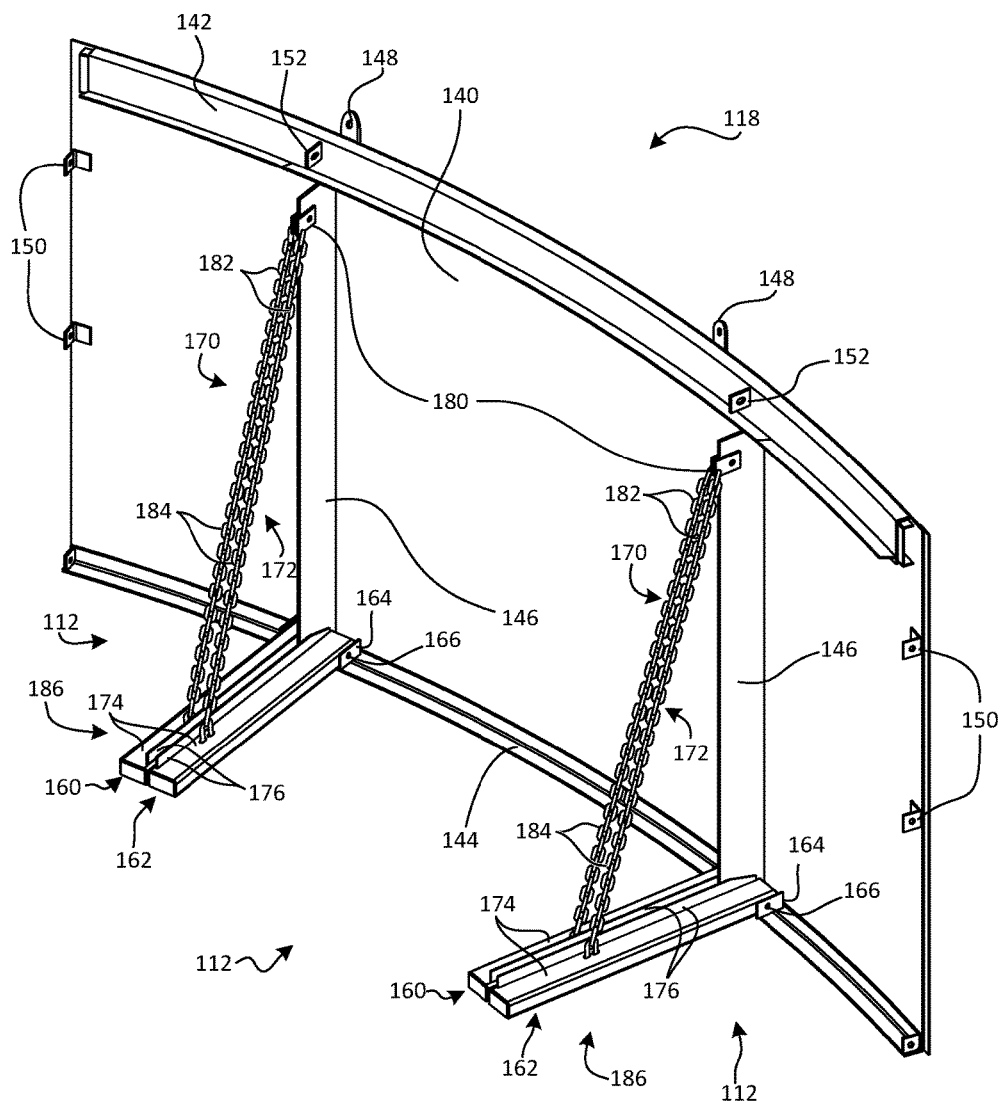
FIG. 4 is a perspective view of a portion of the side wall assembly of the processing tank of FIG. 1.

FIG. 4 is a perspective view of a portion of the side wall assembly 108 of the processing tank 100 of FIG. 1, showing one side wall panel 118, along with one of the ballast support assemblies 112 plus the adjacent halves (to the left and to the right) of two adjoining ballast support assemblies 112. As mentioned previously, the side wall 128 may retain two of the ballast blocks 132 (not shown in FIG. 4) for each side wall panel 118. One of the ballast blocks 132 may be retained at the center of the side wall panel 118 of FIG. 4, and two more ballast blocks 132 may be retained by the side wall panel 118 of FIG. 4, in combination with the two adjoining side wall panels 118 (not shown) installed on either side of the side wall panel 118 of FIG. 4. The side wall panel 118 of FIG. 4 may be exemplary of all of the side wall panels 118 of the side wall assembly 108; accordingly, if desired, each of the side wall panel 118 may have the same configuration as that of FIG. 4.

Referring to FIGS. 3 and 4, the side wall panel 118 may have a wall portion 140, which may be formed of sheet metal or the like, with an arcuate shape. Additionally, the side wall panel 118 may have a top rail 142 positioned at the upper end of the wall portion 140, and a bottom rail 144 positioned at the lower end of the wall portion 140. The top rail 142 and the bottom rail 144 may both have a generally rectangular cross section formed, for example, from folded sheet metal.

Further, the side wall panel 118 may have two vertical flanges 146 extending vertically from the top rail 142 to the bottom rail 144. Each of the vertical flanges 146 may also be formed of folded sheet metal or the like. The vertical flanges 146 may serve as anchoring points for the ballast support assemblies 112, which may, in turn, support the ballast blocks 132.

In addition to the top rail 142, the bottom rail 144, and the vertical flanges 146, the side wall panel 118 may have a plurality of attachment flanges that facilitate attachment of the side wall panel 118 to adjacent components, thereby facilitating assembly of the system 102. The attachment flanges are most clearly seen in FIG. 4. The side wall panel 118 may have four side attachment flanges 150 (two on each side) that can be secured to corresponding side attachment flanges 150 (not shown) on the adjacent side wall panels 118. The side wall panel 118 may also have two cover attachment flanges 152 that are attachable to one or two corresponding cover panels 116 of the cover assembly 106. Further, the side wall panel 118 may optionally have one or more pick point flanges 148 that can be, for example, secured to a crane cable or other flexible member to enable movement and orientation of the side wall panel 118.

As mentioned previously, sliders 154, 156 attached to the side wall 128 may slidably engage the slide guide assembly 110. In one embodiment, the sliders 154, 156 may comprise a top slider 154 secured to the cover 126, and a bottom slider 156 secured to the bottom of the side wall panel 118. The top slider 154 and the bottom slider 156 are most clearly seen in FIG. 3 and may both slidably engage a slide guide assembly 110 having a plurality of slide guides 111. Each slide guide 111 may comprise, for example, an I-beam, a beam, a rail or other structure shaped to engage the top slider 154 and the bottom slider 156 such that the slider assemblies 154, 156 may move vertically along the slide guide assembly 110. Like the cover panels 116 and the side wall panel 118, multiple top sliders 154, bottom sliders 156 and slide guides 111 may be distributed about the interior surface 120 of the outer wall 104 and used to permit the side wall 128 to slide, as a unit, upward or downward relative to the slide guide assembly 110 and outer wall 104. This sliding motion may be accomplished through the use of roller bearings and/or other low-friction mechanisms known in the art. As indicated in FIGS. 1-2, a slide guide assembly 110 may be secured to the interior surface 120 of the outer wall 104. Further, as shown in FIG. 2, the illustrated system 102 may include a floor 190.

As also shown in FIGS. 1-3, the cover panel 116 shown in the section view of FIG. 3 may have an aperture 158 that is centered over the location at which the ballast block 132 is to be retained by the ballast support assembly 112. The aperture 158 may thus be properly positioned for a flexible member, such as the lower end of a cable of a crane, gantry, or other lifting device, to pass through the aperture 158 to lift the ballast block 132 into position, as will be shown and described subsequently. The flexible members could, for example, comprise a chain or cable made of metal and/or another type of material.

Referring once again to FIG. 3, the ballast support assemblies 112 may have a first arm 160 and a second arm 162. The section view of FIG. 3 bisects the ballast support assembly 112 at the center of the side wall panel 118; thus, only the first arm 160 of the ballast support assembly 112 is visible in FIG. 3. The first arm 160 and the second arm 162 may each be pivotably connected to the corresponding side wall panel 118 by a pin support flange 164 (labeled with reference numerals and shown only in FIGS. 4 and 6) and a pin 166 (labeled with reference numerals only in FIGS. 4 and 6). The pin support flanges 164 may each be secured to the adjoining wall portion 140 and the adjoining bottom rail 144 such that the pin support flange 164 are generally parallel to their adjoining vertical flanges 146. Each pin 166 may be cantilevered between one of the vertical flanges 146 and one of the adjoining pin support flanges 164. Each of the first arm 160 and the second arm 162 may have, at its proximal end, a hole (not shown) through which the corresponding pin 166 passes such that the first arm 160 or second arm 162 is rotatable about the pin 166.

In addition to the first arm 160 and the second arm 162, the ballast support assembly 112 may have a clip 168 couplable to the corresponding vertical flange 146, as shown in FIG. 3. The clips 168 may be used to hold the ballast support assembly 112 in a retracted configuration, as will be described in greater detail subsequently. Each of the clips 168 may, if desired, be pivotably coupled to the corresponding vertical flange 146 so that the clips 168 can rotate into or out of engagement with the distal ends of the first arm 160 and the second arm 162. The clips 168 are optional and, in one embodiment, may be omitted.

Further, the ballast support assembly 112 may have a first flexible member secured to the distal end of the first arm 160 to restrict pivoting of the first arm 160 below a horizontal orientation, and a second flexible member secured to the distal end of the second arm 162 to restrict pivoting of the second arm 162 below the horizontal orientation. The flexible members may have a wide variety of configurations, including but not limited to cords, ropes, chains, cables, and the like. In the present embodiment, the first and second flexible members may take the form of a first chain 170 and a second chain 172, respectively.

Each of the first arm 160 and the second arm 162 may have a beam 174 and a lip 176, as best seen in FIG. 4. Each beam 174 and lip 176 may be secured together such that lip 176 extends upward from the outward edge of the beam 174, relative to the final ballast location of the ballast block 132 that will rest on the beam 174. Hence, for each pair of the first arm 160 and the second arm 162, the beams 174 may bear the weight of the associated ballast block 132, and the lips 176 may retain the associated ballast block 132 in the space centered above the first arm 160 and the second arm 162. The angulation of the first arm 160 and the second arm 162 toward the center of the processing tank 100 may help to ensure that the ballast block 132 cannot be moved off of the associated first arm 160 and second arm 162 without interference from the lips 176 of the first arm 160 and the second arm 162. The lips 176 of the first arm 160 and the second arm 162 may also be oriented toward the center of the processing tank 100 to capture the generally trapezoidal shape of the ballast block 132, as will be shown and described subsequently. In one embodiment, the beam 174 is a box beam 174, although the beam 174 may comprise other types of beams or support structures.

The ballast support assembly 112 may further have a pair of flexible member couplings 180 that secure the first chain 170 and the second chain 172 to the side wall panel 118. As shown, a flexible member coupling 180 may be secured to each vertical flange 146. Each flexible member coupling 180 may serve as an anchoring point for the first arm 160 of one of the ballast support assemblies 112 and the adjacent second arm 162, i.e., the second arm 162 of the adjoining ballast support assembly 112 (for example, the first arm 160 of the ballast support assembly 112 in the center of the side wall panel 118 in FIG. 4, and the second arm 162 of the ballast support assembly 112 to the right in FIG. 4).

Each of the flexible members (e.g., in the embodiment of FIGS. 3 and 4, each of the first chain 170 and the second chain 172), may have a proximal end 182 and a distal end 184. Each of the proximal ends 182 may be secured to the corresponding flexible member coupling 180. Each of the distal ends 184 may be secured to the corresponding first arm 160 or second arm 162. More specifically, the distal end 184 of each first chain 170 may be secured to the corresponding first arm 160, and the distal end 184 of each second chain 172 may be secured to the corresponding second arm 162. The distal ends 184 may be secured proximate the distal ends of the first arms 160 and the second arms 162. As shown in FIG. 3, each first arm 160 and each second arm 162 (labeled and shown only in FIG. 4) may have a horizontal orientation 186 and an upwardly-angled orientation 188 (shown in phantom). When the first arm 160 and the second arm 162 are in the horizontal orientation 186, the ballast support assembly 112 is in a deployed configuration in which the ballast support assembly 112 is configured to retain the associated ballast block 132 in its final ballast location. When the first arm 160 and the second arm 162 are in the upwardly-angled orientation 188, the ballast support assembly 112 is in a retracted configuration in which the adjoining ballast support assembly 112 does not impede the substantially vertical motion of the ballast block 132 from an initial ballast location to the final ballast location. In the initial ballast location, the ballast block 132 may rest on a floor 190 of the processing tank 100 beneath the ballast support assembly 112.

Accordingly, in the horizontal orientation 186, the first arm 160 and the second arm 162 may be positioned to retain the corresponding ballast block 132 in its final ballast location 216. Further, with the first arm 160 and the second arm 162 of a ballast support assembly 112 in the horizontal orientation 186, the corresponding first chain 170 and second chain 172 may be under tension between the flexible member couplings 180 to which they are attached at their proximal ends 182, and the corresponding attachment points to which they are attached to the first arm 160 and the second arm 162 at their distal ends 184. Thus, the first chain 170 may exert upward force on the first arm 160 to keep the first arm 160 from rotating below the horizontal orientation 186. Similarly, the second chain 172 may exert upward force on the second arm 162 to keep the second arm 162 from rotating below the horizontal orientation 186.

In the upwardly-angled orientation 188, the first arm 160 and the second arm 162 may be positioned to lie proximate the wall portion 140 of the side wall panel 118 such that the first arm 160 and the second arm 162 are generally displaced from the vertical path to be followed by the ballast block 132 as the ballast block 132 is elevated from the initial ballast location to the final ballast location. Notably, in the upwardly-angled orientation 188, the first arm 160 and the second arm 162 may also not impede further upward motion of the ballast block 132 from the final ballast location to a deployment ballast location above the final ballast location. Motion to the deployment ballast location may permit the ballast support assembly 112 to deploy by moving from the retracted configuration to the deployed configuration, as will be shown and described in connection with FIGS. 5A-5F.

In the upwardly-angled orientation 188, the first arm 160 and the second arm 162 may be positioned to lie proximate the wall portion 140 of the side wall panel 118 such that the first arm 160 and the second arm 162 are generally displaced from the vertical path to be followed by the ballast block 132 as the ballast block 132 is elevated from the initial ballast location to the final ballast location. Notably, in the upwardly-angled orientation 188, the first arm 160 and the second arm 162 may also not impede further upward motion of the ballast block 132 from the final ballast location to a deployment ballast location above the final ballast location. Motion to the deployment ballast location may permit the ballast support assembly 112 to deploy by moving from the retracted configuration to the deployed configuration, as will be shown and described in connection with FIG. 5.

FIGS. 5A-5F are side elevation views of one of the ballast support assemblies 112 of the processing tank 100 of FIG. 1, with the ballast block 132 in various locations. FIGS. 5A-5F illustrate how the ballast block 132 may be moved from the initial ballast location to the final ballast location through the use of a flexible member 200, such as the cable of a crane, hoist, gantry, or other lifting device. The flexible member 200 may have a coupling 202 at its lower end. The flexible member 200 is shown disposed within an aperture 158 in the cover 126. Since FIGS. 5A-5F are section views like that of FIG. 3, only the first arm 160 and the first chain 170 are shown. In each of FIGS. 5A-5F, the second arm 162 and the second chain 172 may follow the configuration and orientation of the first arm 160 and the first chain 170, respectively.

The cover 126 (including the cover panels 116), the side wall 128 (including side wall panels 118), the slide guide assembly 110, the sliders 154, 156, the ballast support assemblies 112, and the various other components may be assembled to formulate the system 102, as illustrated, for example, in FIGS. 1 and 2. This assembly may advantageously be performed before the ballast blocks 132 are moved to their final ballast locations so that the processing tank 100 will have the structural strength and rigidity needed to support the ballast blocks 132. Thus, for each ballast block 132, the coupling 202 of the flexible member 200 may need to be lowered through the cover 126 above the ballast block 132. This may be done by inserting the coupling 202 of the flexible member 200 through the aperture 158 in the cover panel 116 above the ballast block 132 and lowering it until the coupling 202 can be coupled to the ballast block 132. Thus, the associated crane, hoist, gantry, or other lifting device may be able to exert substantially vertical force to lift each ballast block 132, with the cover 126 in place above the ballast support assemblies 112.

FIG. 5A illustrates one of the ballast support assemblies 112 in the deployed configuration with the ballast block 132 in the initial ballast location 210 beneath the ballast support assembly 112. As mentioned previously, the ballast block 132 may initially, for example, rest on the floor 190 of the processing tank 100. FIG. 5A is not necessarily to scale, as the initial ballast location 210 may be vertically displaced from the ballast support assembly 112 by a greater distance than that shown in FIG. 5A. The coupling 202 of the flexible member 200 has been coupled to the ballast block 132 in preparation for lifting the ballast block 132 toward the ballast support assembly 112.

The weight of the first arm 160 and the second arm 162 may tend to pivot the first arm 160 and the second arm 162 into the horizontal orientation 186 as shown in FIG. 5A. Thus, the ballast support assembly 112 may reside in the deployed configuration in the absence of external force urging the first arm 160 and the second arm 162 toward the upwardly-angled orientation 188.

FIG. 5B illustrates the ballast support assembly 112 in a partially-retracted configuration after some upward motion of the ballast block 132. The ballast block 132 has been elevated until the outer top corner of the ballast block 132 has made contact with the first arm 160 and the second arm 162. In response to contact from the ballast block 132, the first arm 160 and the second arm 162 have pivoted to angle upward. Thus, the first arm 160 and the second arm 162 are in an orientation between the horizontal orientation 186 and the upwardly-angled orientation 188. Consequently, the ballast support assembly 112 may be in a configuration between the deployed configuration and the retracted configuration.

The weight of the first arm 160 and the second arm 162 may exert some force against the ballast block 132 that urges the ballast block 132 to move slightly inward (i.e., toward the center of the processing tank 100). However, no horizontal force need be applied to the ballast block 132 to correct this motion; rather, the tension force applied by the flexible member 200, alone, may be sufficient to properly position the ballast block 132, as will be shown in connection with FIGS. 5C-5F.

FIG. 5C illustrates the ballast support assembly 112 in the retracted configuration after further upward motion of the ballast block 132 into a retraction ballast location 212. As shown, the further upward motion of the ballast block 132 has exerted additional force on the first arm 160 and the second arm 162 to urge the first arm 160 and the second arm 162 into the upwardly-angled orientation 188. In the upwardly-angled orientation 188, the first arm 160 and the second arm 162 may not significantly impede further vertical motion of the ballast block 132. As in FIG. 5B, in the retraction ballast location 212 shown in FIG. 5C, the ballast block 132 may be displaced slightly toward the center of the processing tank 100 due to the force exerted on the ballast block 132 by the weight of the first arm 160 and the second arm 162.

FIG. 5D illustrates the ballast support assembly 112 after further upward motion of the ballast block 132 into a deployment ballast location 214 in which the ballast block 132 does not interfere with motion of the ballast support assembly 112 from the retracted configuration back to the deployed configuration. The deployment ballast location 214 may be above the initial ballast location 210 and the retraction ballast location 212. In the deployment ballast location 214, the ballast block 132 may have moved vertically above the distal ends of the first arm 160 and the second arm 162, and may thus exert no force on the first arm 160 and the second arm 162. Thus, the first arm 160 and the second arm 162 may, due to the operation of gravity, pivot back toward the horizontal orientation 186. In FIG. 5D, the first arm 160 and the second arm 162 have begun this motion, and are thus in an orientation between the horizontal orientation 186 and the upwardly-angled orientation 188, as in FIG. 5B.

Further, in the deployment ballast location 214, the first arm 160 and the second arm 162 may not exert further force against the ballast block 132. Hence, the ballast block 132 may be free to move back outward (away from the center of the processing tank 100), and may even rest against the interior of the side wall panel 118.

FIG. 5E illustrates the ballast support assembly 112 after the ballast support assembly 112 has moved back to the deployed configuration. The ballast block 132 may still be in the deployment ballast location 214 as in FIG. 5D. As shown, the first arm 160 and the second arm 162 may have returned, due to the operation of gravity, back to the horizontal orientation 186. The first chain 170 and the second chain 172 may again be tensioned such that the first arm 160 and the second arm 162 are unable to pivot downward below the horizontal orientation 186. The ballast support assembly 112 may thus be ready to receive the ballast block 132 in the final ballast location 216.

FIG. 5F illustrates the ballast support assembly 112 in the deployed configuration, with the ballast block 132 in the final ballast location 216. In the final ballast location 216, the ballast block 132 may rest on the first arm 160 and the second arm 162. The first chain 170 and the second chain 172 may be tensioned to keep the first arm 160 and the second arm 162 from pivoting below the horizontal orientation 186, and may generally bear the weight of the ballast block 132.

Advantageously, the construction crew that installs the ballast blocks 132 may not be required to take any steps to exert force on the ballast blocks 132, except for that provided by the crane, hoist, gantry, or other lifting device. Motion of the ballast support assembly 112 from the deployed configuration to the retracted configuration, and then back to the deployed configuration, may all happen incident to the ensuing vertical motion of the ballast block 132. Although some horizontal motion of the ballast block 132 may occur as a result of its interaction with the ballast support assembly 112, such horizontal motion is not necessary for motion of the ballast block 132 to the final ballast location 216.

Thus, the ballast support assembly 112 may not significantly block vertical motion of the ballast block 132 from the initial ballast location 210 to the final ballast location 216. As mentioned previously, the final ballast location 216 may be offset substantially directly vertically from the initial ballast location 210. In this application, "offset substantially directly vertically" means that the vast majority of the offset between the initial ballast location 210 and the final ballast location 216 is vertical, not horizontal. However, "offset substantially directly vertically" does not require that there be no horizontal component to the offset between the initial ballast location 210 and the final ballast location 216.

In one example, the offset between the initial ballast location 210 and the final ballast location 216 may have a horizontal component and a vertical component. The horizontal component may be, in magnitude, 10% or less of the magnitude of the vertical component. More specifically, in various embodiments, the horizontal component may be, in magnitude, 5% or less of the magnitude of the vertical component. Yet more specifically, the horizontal component may be, in magnitude, 2% or less of the magnitude of the vertical component.

In this application, a structure that does "not significantly block vertical motion" of a ballast block from a first location to a second location is a structure that either is positioned to avoid contact with the ballast block as it moves vertically from the first location to the second location, or is configured to be movable, in response to contact with the ballast block as the ballast block moves vertically from the first location toward the second location into a configuration in which it does not block motion of the ballast block to the second location. Contact with the structure may cause the ballast block to move horizontally, but the horizontal motion of the ballast block incident to contact with the structure is small compared to the horizontal size of the ballast block. In one example, the ballast block 132 may move horizontally as it contacts the ballast support assembly 112 to move the ballast support assembly 112 into the retracted configuration, as illustrated in FIGS. 5B and 5C.

In one example, this horizontal motion may be less than 50% of the depth of the ballast block 132 along the direction in which the horizontal motion occurs (for example, this motion may be radial relative to the processing tank 100, as shown in FIGS. 5B and 5C). More specifically, this horizontal motion may be less than 20% of the depth of the ballast block 132 along the direction in which the horizontal motion occurs. Yet more specifically, this horizontal motion may be less than 10% of the depth of the ballast block along the direction in which the horizontal motion occurs. In other words, in various embodiments, the ballast support assembly 112 may not require a lateral motion of the ballast block 132 greater than 50%, 30%, 26%, 20%, 10% or 6%, respectively, of the ballast block width, measured from the side of the ballast block 132 nearest the side wall assembly 108 to the side of the ballast block 132 farthest from the side wall assembly 108, during motion of the ballast block 132 from the initial ballast location 210 to the deployment ballast location 214.

In further examples, the horizontal motion may be determined by the geometry of the ballast support assembly 112. More specifically, the length of the first arm 160 and the second arm 162, and the maximum angle (above the horizontal) to which the first arm 160 and the second arm 162 can be elevated in the upwardly-angled orientation 188, may determine the magnitude of horizontal motion that occurs. More precisely, the horizontal motion of the ballast block 132 required to enable the ballast block 132 to ascend past the ballast support assembly 112, in the retracted configuration, may be equal to the length of the first arm 160 and the second arm 162 multiplied by the cosine of the angle, above the horizontal, at which the first arm 160 and the second arm 162 are disposed in the upwardly-angled orientation 188. In the event that the first arm 160 and the second arm 162 are different lengths, or the first arm 160 and the second arm 162 are disposed at different angles in the upwardly-angled orientation 188, the horizontal motion may be calculated for each of the first arm 160 and the second arm 162, and the larger of the two may be deemed to be the maximum horizontal motion of the ballast block 132.

By way of further example, the first arm 160 and the second arm 162 may be of equal lengths, and may both be disposed at an angle ranging from 75° to 86° in the upwardly-angled orientation 188. At the 75° angle, the cosine of 75° is about 0.26, meaning that the horizontal motion of the ballast block 132 will be about 26% of the length of the first arm 160 and the second arm 162. At the 86° angle, the cosine of 86° is about 0.07, meaning that the horizontal motion of the ballast block 132 will be about 7% of the length of the first arm 160 and the second arm 162. Thus, the horizontal motion of the ballast block 132, during its ascent from the initial ballast location 210 to the deployment ballast location 214, may, in one embodiment, range from 7% to 26% of the length of the first arm 160 and the second arm 162.

As illustrated in FIGS. 5A and 5F, the aperture 158 in the cover 126 is within a direct vertical extension 131, 135 of both the initial ballast location 210 and the final ballast location 216. The vertical extension 131, 135 comprises a vertical extension directly above the outer boundaries of the ballast block 132 (i.e., the outer boundaries of the width and depth of the ballast block 132, as seen from the side perspective of FIGS. 5A and 5F). As illustrated in these figures, the outer boundaries of the aperture 158 (i.e., the outer boundaries of the width and depth of the aperture 158) may be substantially smaller than the outer boundaries of the ballast block 132. Accordingly, in one embodiment, the aperture 158 is within a one-quarter vertical extension 133, 137 of both the initial ballast location 210 and the final ballast location 216. The one-quarter vertical extension 133, 137 involves a vertical extension above the initial and final ballast locations 210, 216 centered above the ballast block 132 but one-quarter in size along the depth and width of the ballast block 132. In alternative embodiments, the aperture 158 is disposed only within a vertical extension 131, 135 or a quarter vertical extension 133, 137 of either the initial ballast location 210 or the final ballast location 216.

In one embodiment, the initial ballast location 210 is the location at which the ballast block 132 is positioned when the flexible member 200 is secured to the ballast block 132 immediately prior to elevating the ballast block 132 during the positioning process. The final ballast location 216 comprises the location of the ballast block 132 when the ballast block 132 comes to rest on the first arm 160 and second arm 162 with these arms 160, 162 in the horizontal position.

Figure 6:
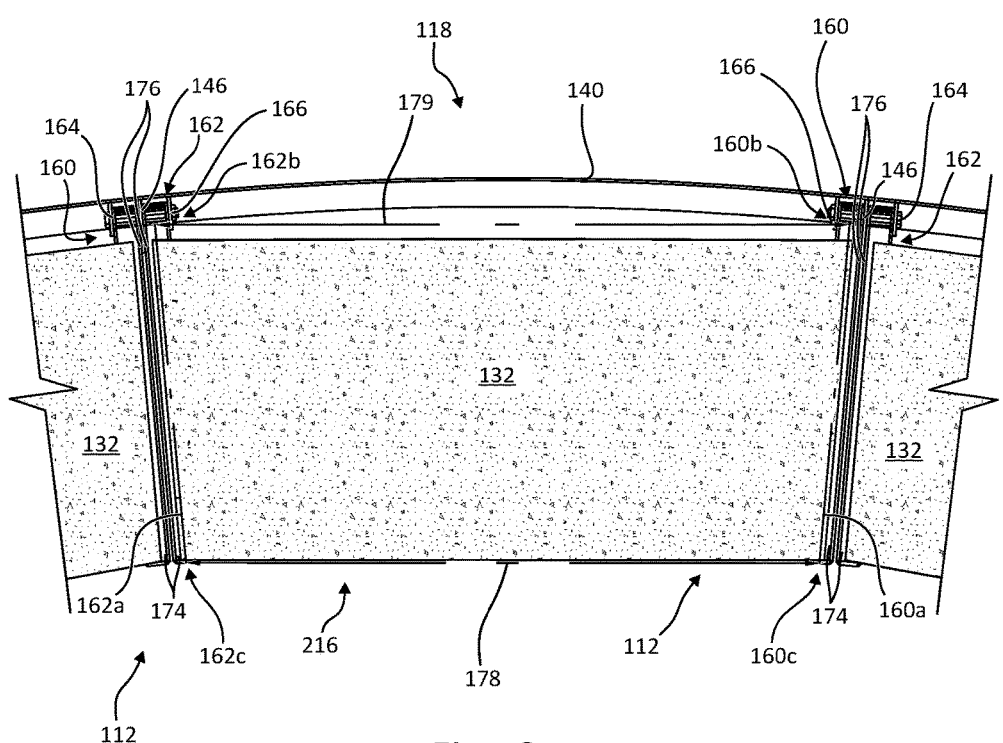
FIG. 6 is a top elevation view of various ballast support assemblies and ballast blocks with the ballast blocks in the final ballast location.

FIG. 6 is a top elevation view of the ballast support assembly 112 and ballast block 132 of FIGS. 5A-5F, with the ballast block 132 in the final ballast location 216. As shown, the ballast block 132 may rest on the beams 174 of the first arm 160 and the second arm 162, between the lip 176 of the first arm 160 and the lip 176 of the second arm 162.

In the final ballast location 216, significant horizontal motion of the ballast block 132 may be substantially prevented. More specifically, the ballast block 132 may be retained on the beams 174 by the lips 176, which may act to prevent significant lateral motion of the ballast block 132, from the perspective shown in FIG. 6. As shown, the first arm 160 and the second arm 162 are not parallel to each other, since both may be oriented generally radially (i.e., parallel with a radius of the processing tank 100). Thus, the lips 176 and the adjoining ballast blocks 132 may also prevent the ballast block 132 from moving radially, toward the center of the processing tank 100. The wall portion 140 of the corresponding side wall panel 118 may limit motion of the ballast block 132 away from the center of the processing tank 100.

In spite of these restrictions on horizontal motion from the final ballast location 216, it can be seen in the view of FIG. 6 that the ballast block 132 may be moved vertically into position, even if the ballast blocks 132 to either side have already been installed. The first arm 160 and the second arm 162 of each adjacent pair (i.e., the first arm 160 and the second arm 162 attached to the same vertical flange 146) may be independently pivotable; thus, motion of each ballast support assembly 112 between its deployed and retracted configurations may be independent of the configurations of the adjoining ballast support assemblies 112.

Notably, the first arm 160 and the second arm 162 may be longer or shorter than the depth of the ballast block 132 in the radial direction (i.e., up and down in the view of FIG. 6). Further, due to the trapezoidal shape of the ballast block 132, the side edges of the ballast block 132 (the edges on the left and right in the view of FIG. 6) may be longer than the depth of the ballast block 132 in the radial direction. This is because the side edges of the ballast block 132 are not parallel to the depth in the radial direction.

In the exemplary embodiment of FIG. 6, the first arm 160 and the second arm 162 may be shorter than the ballast block 132. As long as the first arm 160 and the second arm 162 extend radially past the center of gravity of the ballast block 132, the ballast block 132 may be expected to remain in place on the first arm 160 and the second arm 162, in the final ballast location 216. Increasing the length of the first arm 160 and the second arm 162 may advantageously provide additional stability, at the cost of requiring additional horizontal motion of the ballast block 132 during installation of the ballast block 132, per the formula provided previously. As also illustrated in FIG. 6, the first arm 160 may comprise a longitudinal axis 160*a* extending between a radially outward end 160*b* and a radially inward end 160*c*. The second arm 162 may also comprise a longitudinal axis 162*a* extending between a radially outward end 162*b* and a radially inward end 162*c*. As illustrated, the longitudinal axis 160*a* of the first arm 160 may be in a nonparallel orientation with respect to the longitudinal axis 162*a* of the second arm 162 when the first arm 160 is in a horizontal orientation and the second arm 162 is in a second horizontal orientation, as illustrated in FIG. 6. In one embodiment, as once again illustrated in FIG. 6, when the first arm 160 is in the first horizontal orientation and the second arm is in the second horizontal orientation, the radially inward end 160*c* of the first arm 160 is separated from the radially inward end 162*c* of the second arm by a first distance 178, and the radially outward end 160*b* of the first arm 160 is separated from the radially outward end 162*b* of the second arm 162 by a second distance 179. As shown, the second distance 179 may be greater than the first distance 178.

It is understood that any specific order or hierarchy of steps in any disclosed process is an example of a sample approach. Based upon design preferences, it is understood that the specific order or hierarchy of steps in the processes may be rearranged while remaining within the scope of the present disclosure. The accompanying method claims present elements of the various steps in a sample order, and are not meant to be limited to the specific order or hierarchy presented.

The previous description of the disclosed aspects is provided to enable any person skilled in the art to make or use the present disclosure. Various modifications to these aspects will be readily apparent to those skilled in the art, and the generic principles defined herein may be applied to other aspects without departing from the scope of the disclosure. Thus, the present disclosure is not intended to be limited to the aspects shown herein but is to be accorded the widest scope consistent with the principles and novel features disclosed.

What is claimed is:

1. A system for facilitating construction of a processing tank comprising a first ballast block, the system comprising:
   a cover assembly that can be assembled to form a cover that defines an upper barrier for the processing tank;
   a side wall assembly that can be assembled to form a side wall connectable to the cover; and
   a first ballast support assembly comprising:
      a first arm connectable to the side wall such that, when the first arm is pivotably connected to the side wall, the first arm is pivotable between a first horizontal orientation and a first upwardly-angled orientation;
      a second arm pivotably connectable to the side wall such that, when the second arm is pivotably connected to the side wall, the second arm is pivotable between a second horizontal orientation and a second upwardly-angled orientation, wherein, when connected to the side wall, the first arm and the second arm each are independently pivotable;
      a first flexible member comprising a first proximal end connectable to the side wall and a first distal end connectable to the first arm, wherein, with the first arm in the first horizontal orientation when the first arm is connected to the side wall and the first proximal end of the first flexible member is connected to the side wall and the first distal end of the first flexible member is connected to the first arm, the first flexible member is tensioned to restrict pivoting of the first arm below the first horizontal orientation; and
      a second flexible member comprising a second proximal end connectable to the side wall and a second distal end connectable to the second arm, wherein, with the second arm in the second horizontal orientation when the second arm is connected to the side wall, and the second proximal end of the second flexible member is connected to the side wall, and the second distal end of the second flexible member is connected to the second arm, the second flexible member is tensioned to restrict pivoting of the second arm below the second horizontal orientation;
   wherein, with the first arm in the first upwardly-angled orientation and the second arm in the second upwardly-angled orientation, the first ballast support assembly does not significantly block vertical motion of the first ballast block from an initial ballast location to a final ballast location;
   wherein the final ballast location is offset substantially directly vertically from the initial ballast location;
   wherein, with the first arm in the first horizontal orientation and the second arm in the second horizontal orientation, the first ballast support assembly is positioned to retain the first ballast block in the final ballast location.

2. The system of claim 1, when connected to the side wall, each of the first arm and the second arm comprises a radially inward end, a radially outward end, and a longitudinal axis extending between the radially inward end and the radially outward end, the radially outward end being positioned closer to the side wall than the radially inward end, wherein when the first arm is in the first horizontal orientation and the second arm is in the second horizontal orientation, the longitudinal axis of the first arm is in a nonparallel orientation with respect to the longitudinal axis of the second arm.

3. The system of claim 2, wherein, when the first arm is in the first horizontal orientation and the second arm is in the second horizontal orientation, the radially inward end of the first arm is separated from the radially inward end of the second arm by a first distance, and the radially outward end of the first arm is separated from the radially outward end of the second arm by a second distance, the second distance being greater than the first distance.

4. The system of claim 3, wherein the first arm comprises a first beam and a first lip, the first lip extending away from the first beam and being positioned on the first beam to limit movement of the first ballast block when the first ballast block is positioned on the first beam, and the second arm comprising a second beam and a second lip, the second lip extending away from the second beam and being positioned on the second beam to limit movement of the first ballast block when the first ballast block is positioned on the second beam, wherein each of the first and second lips are elongate.

5. A method for constructing the processing tank of claim 1, the method comprising:
   at least partially assembling the cover assembly to form at least part of the cover that defines the upper barrier for the processing tank;
   at least partially assembling the side wall assembly to form at least part of the side wall connectable to the cover;
   raising the first ballast block from the initial ballast location to a retraction ballast location;
   moving the first ballast support assembly from a deployed configuration to a retracted configuration;
   raising the first ballast block from the retraction ballast location to a deployment ballast location;
   moving the first ballast support assembly from the retracted configuration back to the deployed configuration; and
   lowering the first ballast block from the deployment ballast location to the final ballast location such that the first ballast support assembly retains the first ballast block in the final ballast location.

6. The method of claim 5, wherein moving the first ballast support assembly from the deployed configuration to the retracted configuration comprises, in response to moving the first ballast block to the retraction ballast location, abutting the first ballast support assembly with the first ballast block to move the first ballast support assembly to the retracted configuration.

7. The method of claim 6, wherein the first ballast support assembly is movably connectable to the side wall such that gravity exerts force on the first ballast support assembly tending to move the first ballast support assembly from the retracted configuration to the deployed configuration, wherein moving the first ballast support assembly from the retracted configuration back to the deployed configuration comprises, in response to raising the first ballast block from the retraction ballast location to the deployment ballast location, withdrawing the first ballast block from abutment with the first ballast support assembly to permit motion of the first ballast support assembly back to the deployed configuration.

8. The method of claim 5, wherein the cover assembly comprises an aperture, wherein at least partially assembling the cover assembly comprises positioning the aperture at a location within a vertical extension of the initial ballast location and the final ballast location, the method further comprising, prior to raising the first ballast block from the initial ballast location to the retraction ballast location:

lowering a distal end of a third flexible member through the aperture; and securing the distal end of the third flexible member to the first ballast block;

wherein raising the first ballast block from the initial ballast location to the retraction ballast location comprises tensioning the third flexible member to pull the first ballast block substantially vertically to the final ballast location.

9. The method of claim 5, wherein the first ballast support assembly comprises the first arm and the first flexible member, wherein moving the first ballast support assembly from the deployed configuration to the retracted configuration comprises moving the first arm from the first horizontal orientation, in which the first flexible member is tensioned to restrict pivoting of the first arm below the first horizontal orientation, to the first upwardly-angled orientation.

10. The method of claim 9, wherein the first ballast support assembly further comprises the second arm and the second flexible member, wherein moving the first ballast support assembly from the deployed configuration to the retracted configuration comprises moving the second arm from a second horizontal orientation, in which the second flexible member is tensioned to restrict pivoting of the second arm below the second horizontal orientation, to the second upwardly-angled orientation.

11. A system for facilitating construction of a processing tank comprising a first ballast block, the system comprising:

a cover assembly that can be assembled to form a cover that defines an upper barrier for the processing tank;

a side wall assembly that can be assembled to form a side wall securable to the cover; and a first ballast support assembly movably connectable to the side wall such that, when the side wall is oriented vertically and when the first ballast assembly is connected to the side wall, the first ballast support assembly has, relative to the side wall, a retracted configuration and a deployed configuration, wherein the first ballast support assembly comprises a first arm and a second arm, each of the first arm and the second arm being pivotably connectable to the side wall, and wherein, when connected to the side wall, the first and the second arms are each independently pivotable;

wherein, in the retracted configuration, the first ballast support assembly does not significantly block vertical motion of the first ballast block from an initial ballast location to a final ballast location;

wherein the final ballast location is offset substantially directly vertically from the initial ballast location;

wherein, in the deployed configuration, the first ballast support assembly is positioned to retain the first ballast block in the final ballast location.

12. The system of claim 11, wherein the cover assembly comprises a plurality of cover panels, each of which has a generally sectoral shape, wherein the cover panels are attachable together to form the cover such that the cover has a generally circular shape, wherein the side wall assembly comprises a plurality of wall panels, each of which has a generally arcuate shape, wherein the wall panels are attachable together to form the side wall such that the side wall has a generally tubular shape.

13. The system of claim 12, further comprising:

a slide guide assembly comprising a plurality of slide guides securable to an outer wall;

a plurality of sliders securable to the side wall and/or the cover, wherein each of the plurality of sliders may slidably engage at least one of the slide guides wherein the cover and the first ballast support assembly can be coupled to the side wall such that the cover and the first ballast support assembly move vertically with the side wall relative to the outer wall when the cover and the first ballast support assembly are secured to the side wall and when each of the plurality of sliders are secured to the side wall and/or the cover and slidably engage at least one of the slide guides.

14. The system of claim 12, further comprising a plurality of additional ballast support assemblies, each of which is movably connectable to the side wall such that, with the side wall oriented vertically, each of the additional ballast support assemblies has the retracted configuration and the deployed configuration relative to an additional ballast block of a plurality of additional ballast blocks of the processing tank.

15. The system of claim 11, wherein the cover assembly comprises an aperture positionable at a location within a vertical extension of both the initial ballast location and the final ballast location such that, with the side wall oriented vertically and the cover assembly secured above the side wall, a distal end of a flexible member lowered through the aperture can lift the first ballast block substantially vertically to move the first ballast block from the initial ballast location to the final ballast location.

16. The system of claim 11, wherein the first ballast support assembly is movably connected to the side wall such that motion of the first ballast block from the initial ballast location to the final ballast location causes the first ballast block to abut the first ballast support assembly to move the first ballast support assembly from the deployed configuration to the retracted configuration.

17. The system of claim 16, wherein the first ballast support assembly is movably connectable to the side wall such that gravity exerts force on the first ballast support assembly tending to move the first ballast support assembly from the retracted configuration to the deployed configuration, wherein the first ballast support assembly is further movably connectable to the side wall such that motion of the first ballast block from the final ballast location to a deployment ballast location above the final ballast location causes the first ballast support assembly to return to the deployed configuration; wherein, in the deployed configuration, the first ballast support assembly is positioned to receive and retain the first ballast block in response to motion of the first ballast block from the deployment ballast location to the final ballast location.

18. The system of claim 11, wherein, when the first arm is connected to the side wall, the first arm is in a first horizontal orientation when the first ballast support assembly is in the deployed configuration, and in a first upwardly-angled orientation when the first ballast support assembly is in the retracted configuration, wherein, when the second arm is connected to the side wall, the second arm is in a second horizontal orientation when the first ballast support assembly is in the deployed configuration, and in a second upwardly-angled orientation when the first ballast support assembly is in the retracted configuration, and wherein, when connected to the side wall, each of the first arm and the second arm comprise a radially inward end, a radially outward end, and a longitudinal axis extending between the radially inward end and the radially outward end, the radially outward end being positioned closer to the side wall than the radially inward end, wherein when the first arm is in the first horizontal orientation and the second arm is in the second horizontal orientation, the longitudinal axis of the first arm is in a nonparallel orientation with respect to the longitudinal axis of the second arm.

19. The system of claim 18, wherein, when the first arm is in the first horizontal orientation and the second arm is in the second horizontal orientation, the radially inward end of the first arm is separated from the radially inward end of the second arm by a first distance, and the radially outward end of the first arm is separated from the radially outward end of the second arm by a second distance, the second distance being greater than the first distance.

20. The system of claim 19, wherein the first arm comprises a first beam and a first lip, the first lip extending away from the first beam and being positioned on the first beam to limit movement of the first ballast block when the first ballast block is positioned on the first beam, and the second arm comprising a second beam and a second lip, the second lip extending away from the second beam and being positioned on the second beam to limit movement of the first ballast block when the first ballast block is positioned on the second beam, wherein each of the first and second lips are elongate.

* * * * *